(12) United States Patent
Hirano et al.

(10) Patent No.: US 6,687,533 B1
(45) Date of Patent: Feb. 3, 2004

(54) MARKERS FOR CT AND MRI IMAGING

(75) Inventors: Hiroyuki Hirano, Funabashi (JP); Naomitsu Takekawa, Tokyo (JP)

(73) Assignee: Alcare Co., Ltd., Tokyo (JP)

( * ) Notice: Subject to any disclaimer, the term of this patent is extended or adjusted under 35 U.S.C. 154(b) by 444 days.

(21) Appl. No.: 09/602,753

(22) Filed: Jun. 23, 2000

(30) Foreign Application Priority Data

Jun. 24, 1999 (JP) .............................. 11-177740

(51) Int. Cl.$^7$ ................................ A61B 5/055
(52) U.S. Cl. ............... 600/426; 600/414; 600/417; 600/429; 424/9.3; 424/9.4; 424/9.411
(58) Field of Search .............. 606/130; 378/205, 378/162, 163, 164, 165, 62, 63, 64, 65; 424/9.3, 9.4, 9.411, 9.321, 9.322, 9.41; 436/173; 600/407, 410, 411, 413, 414, 415, 417, 420, 421, 424, 425, 426, 427, 429, 428, 431, 436

(56) References Cited

U.S. PATENT DOCUMENTS

| | | | | |
|---|---|---|---|---|
| 4,774,957 A | * | 10/1988 | Nambu et al. | 600/414 |
| 4,916,170 A | * | 4/1990 | Nambu et al. | 523/137 |
| 4,951,673 A | * | 8/1990 | Long | 424/9.37 |
| 5,320,100 A | * | 6/1994 | Herweck et al. | 600/431 |
| 5,368,030 A | * | 11/1994 | Zinreich et al. | 600/414 |
| 5,427,099 A | * | 6/1995 | Adams | 600/414 |
| 5,469,847 A | * | 11/1995 | Zinreich et al. | 600/414 |
| 5,682,890 A | * | 11/1997 | Kormos et al. | 600/417 |
| 6,122,541 A | * | 9/2000 | Cosman et al. | 600/426 |
| 6,419,680 B1 | * | 7/2002 | Cosman et al. | 606/130 |

* cited by examiner

Primary Examiner—Eleni Mantis Mercader
(74) Attorney, Agent, or Firm—Adams & Wilks

(57) ABSTRACT

A non-implantable CT and MRI marker has a first component formed of at least one of a silicone resin and a fluorcarbon resin and a second component comprised of at least one of an elastomer and an organogel contained in the first component.

33 Claims, 2 Drawing Sheets

MARKERS FOR CT AND MRI IMAGING

BACKGROUND OF THE INVENTION

1. Field of the Invention

The present invention relates generally to a radiotherapy marker, and more particularly, to a marker used in CT and MRI imaging.

2. Background Information

In the medical treatment of lesions or focuses such as tumors and the like in the brains and bodies of patients, radiotherapy is a widely conducted treatment. In radiotherapy, a radioactive beam is irradiated from outside of the patient's body onto a desired focus. When conducting radiotherapy, it is desirable to minimize the amount of irradiation incident onto normal tissue (cells) while maximizing the amount of radioactive energy irradiated onto concerned focuses or lesions. For this purpose, it is generally necessary to precisely irradiate a low dose radioactive beam onto a focus from multiple directions. In the practice of radiotherapy, it is necessary to first develop a medical treatment plan with respect to irradiation positions, irradiation directions, exposure dose, exposure times and the like. For the purpose of developing such a plan, it is indispensable to map out the size of a concerned focus in the patient's body and the three-dimensional position thereof in a precise manner.

In such medical treatment plans, at the present time, Computed Tomography (CT) imaging using a radioactive beam is typically carried out to investigate the size and position of a focus. In such imaging, a marker is used so that changes in position of the marker and the focus displayed on laminagram images are read and reconfigured to specify the position, size, topography, and the like, of a concerned focus.

Conventionally, as a CT marker, a metallic wire has been employed based on its X-ray absorption characteristics. While this conventional type of marker appears clearly on CT images, a sharp wire may injure a patient and has thus been considered dangerous. In addition, the conventional wire marker becomes rusted after long term service, and accordingly, has poor durability and high fear of contamination. As a result, use of a metallic wire as a CT marker has been deemed far from satisfactory in the art.

In the development of the above-described medical treatment plans, Magnetic Resonance Imaging (MRI) photography is also widely used. In the case of MRI imaging, results of tomography, also using a marker, are reconfigured in the manner described above to specify the size, position, and the like of a concerned focus.

Generally, in MRI there is not so significant a difference between the proton density of normal tissues and that of focuses, while there is a significant difference between their respective relaxation times. This relaxation time has two factors, i.e., longitudinal relaxation (T1) and transverse relaxation (T2), and T1 and T2 are generally of such a nature as to offset signal strength. Consequently, it is necessary to separately obtain images in which T1 is emphasized (T1-weighted spin-echo images) and images in which T2 is emphasized (T2-weighted spin-echo images).

In the prior art, as a marker for T1-weighted spin-echo images, water solutions of margarine, salad oil, paramagnetic materials and so forth have been employed, while water has been employed as a marker for T2-weighted spin-echo images. The markers must thus be changed prior to respective cases of photographing T1-weighted spin-echo images and T2-weighted spin-echo images, which in turn leads to deteriorated precision in the positioning of a concerned focus, and further makes handling markers and photographing complicated and troublesome. These have been the problems associated with the conventional art in the present field.

To overcome these problems, the present inventors have provided markers wherein paramagnetic material is added uniformly into viscous liquid and gel hydrophilic substances, which has enabled photographing both T1- and T2-weighted spin-echo images. The present invention aims at making them easier to use, and gives them even more excellent durability.

SUMMARY OF THE INVENTION

Accordingly, it is an object of the present invention to provide a marker for CT image photographing which is safer and more durable than conventional CT markers and which appears clearly on images based on the preferable absorption thereof.

Another object of the present invention is to provide a marker for CT image photographing, which is safe and durable, and which also outputs high signals in both T1 and T2-weighted spin-echo MRI images and responds to both of them.

It is still another object of the present invention to provide a marker that can be employed for both CT and MRI imaging, which enables one to conduct CT image photographing and MRI (T1, T2) image photographing by use of a single marker.

The present invention has been made on the basis of the knowledge that the present inventors found in their search for a new CT marker to replace the conventional metallic wire, that silicon resin and fluorocarbon resin appeared clearly on CT images.

As a marker for MRI imaging, the inventors also found that elastomer of rubber and so forth, and organogel polyethylene gel and so forth output high signals in response in photographing T1 and T2-weighted spin-echo images, and appear clearly on such images, thereby obtaining an MRI marker having excellent durability.

Still further, a combination of the above CT marker and MRI marker enables the acquisition of clear images in photographing CT as well as T1 and T2 MRI images without mutual image interference. Accordingly, it enables a single marker to be employed in both CT and MRI imaging operations.

BRIEF SUMMARY OF THE INVENTION

DETAILED DESCRIPTION OF THE PREFERRED EMBODIMENTS

In photographing CT images, CT parameters are generally employed, and these CT parameters are determined by the X-ray absorption dose used. These CT parameter values vary from −1000 to +1000, wherein the CT parameter for air is −1000, that for water is 0, and that for a matter which absorbs all is defined as +1000. In general, the CT parameter of bone varies from +300 to +1000, and that of soft tissue is around −80 to −50, while that of brain or liver tissue in normal diagnosis appears from +35 to +100, and that of lung tissue appears from −800 to −700. As a result, it is preferable for a marker to have a CT parameter at least over 0, and preferably over 60.

The CT parameter of the silicon resin mentioned above is from about +130 to +230, and that of the fluorocarbon resin mentioned above appears nearly the same. Therefore, each substance can provide clear images in photographing CT images. In addition, these two resins may be employed together at the same time if desired.

Figure 3:
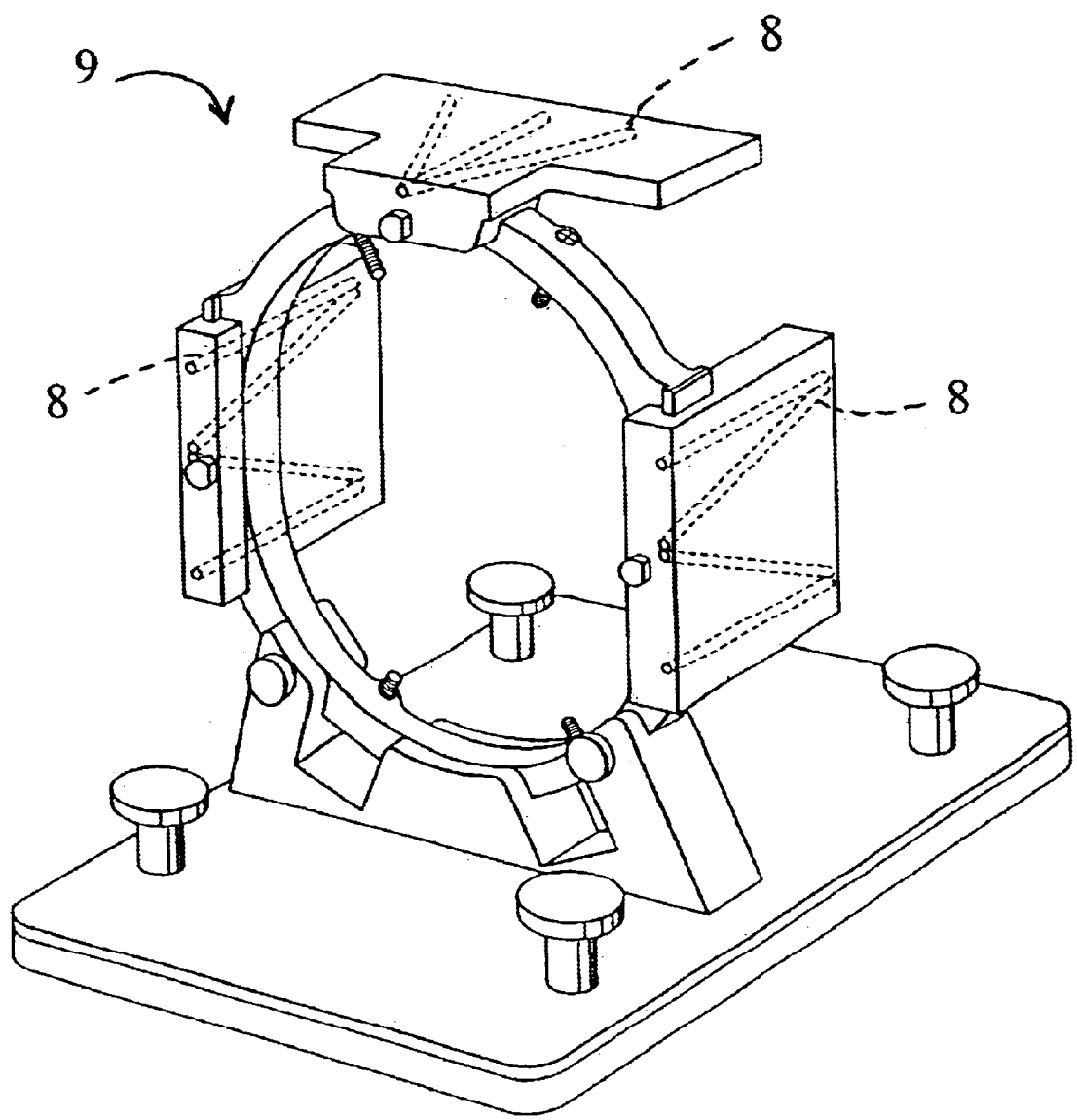
FIG. 3 shows a patient restraint apparatus having insertion holes for accomodating the markers according to the present invention.

It is preferable that these CT markers are normally employed in the form of solid bars with a diameter of about 1–6 mm, and preferably about 2–4 mm, and the shape of such bars in specified length enables their insertion into an insertion hole arranged in a brain stereotactic radiosurgery, brain stereotactic mask, and other types of diagnostic patient restrainers, and to easily position them. For example, as shown in FIG. 3, the markers according to the present invention are configured and shaped to be accomodated into insertion holes 8 of a patient restraint apparatus 9. Further, the markers will not injure patients and will not rust as do conventional wire markers. Therefore, they have excellent durability and safety characteristics. Moreover, these CT markers may be formed into the shape of hollow bars.

In MRI imaging, as a marker to respond to both the above-described T1-weighted spin-echo images and T2-weighted spin-echo images, elastomers are available in single or in combination, such as: elastomers of styrene isoprene styrene copolymer (SIS), styrene ethylene butylene styrene copolymer (SEBS), styrene ethylene propylene styrene copolymer (SEPS), isoprene rubber (IR), isobutylene isoprene rubber (IIR), natural rubber (NR) and so forth. And as organogel, available in single or in combination, there are the organogels polyethylene gel, acrylic gel, urethane gel and so forth. The above-described elastomer and organogel may be used in combination if desired.

The above polyethylene gel is one wherein a plasticizer is mixed into ethylene styrene copolymer. As the plasticizer, there is employed liquid paraffin, mineral oil, phthalic acid plasticizers such as butyl benzyl phthalate (BBP), di-octyle phthalate (DOP), di-butyl phthalate (DBP), di-iso nonyl phthalate (DINP) and so forth, soy bean oil, and fatty acids such as oleic acid, linoleic acid and so forth.

The above acrylic gel is first copolymerized by such main components as 2-ethyl hexyl acrylate, methyl acrylate, methyl methacrylate, butyl acrylate, and so forth, with acrylic acid, methacrylic acid, vinyl acetate and so forth. A plasticizer is added thereto, and crosslinked by chemical compounds such as isocyanate, aziridine, an epoxy, epoxy system, and so forth. The plasticizers used are similar to those employed in the polyethylene gel described above.

The above urethane gel is a gel of urethane resin plasticized by the phthalic acid type plasticizer employed in the polyethylene gel, or a gel of urethane resin polymerized by polyisocyanate and polyole with molecular weight above about 3000.

Examples of these which have been used are, for example, Cosmogel (polyethylene gel of ethylene styrene copolymer plasticized by liquid paraffin, manufactured by Cosmo Instruments Co., Ltd.), Saivinol AT-304 (acrylic gel, manufactured by Saiden Chemical Industry Co., Ltd.), and so forth.

The elastomer and organogel are filled separately or together into a tube or formed into a bar shape by a sheet. The tube or sheet are formed of materials that do not affect the T1- and T2-weighted spin-echo images of MRI, for instance, nylon, polyester, polypropylene, polyvinyl chloride and so forth. The tube or bar having elastomer and organogel may be used conveniently in the same manner as described above in CT image photographing. And they may be formed into a bar shape or the like by use of a mold.

While the present inventors have tried various combinations of elastomers and organogel that may be used as the above MRI marker, and those that may be employed as the above CT marker, the inventors found that the combination attained appropriate X-ray absorption in CT photographing, and output high signals in both T1 and T2 of MRI, and that they thus do not interfere with each other in both CT and MRI imaging.

Namely, the combination marker of the present invention has sufficient sensitivity as a marker for both CT photographing and MRI photographing, when the material for the above MRI marker is filled into a hollow tube formed of a material that may be employed as the above CT marker.

In this case, the material for the MRI marker may be contained by the material for the above CT marker, or both the materials may be laminated, or formed into bar shapes and so forth.

In the CT photographing described above, it is easy to make out the position of a concerned focus but difficult to make out the shape thereof, while in MRI photographing, wherein there is image distortion peculiar to MRI, it is easy to make out the shape and size of a concerned focus, but difficult to make out the position thereof. The use of the above-described combination marker that responds to both CT photographing and MRI photographing enables one to carry out CT photographing with this marker fixed onto a patient, and to then carry out MRI photographing without replacing the marker with another. Accordingly, it is possible to prevent displacement in both the CT and MRI images, and to make out the position, shape and size of a concerned focus in a more precise manner.

In recent years, the development of open magnetic resonance imaging and the advancement of computer software have enabled the acquisition of images wherein distortion of MRI images is revised. In creating synthetic images from these MRI images and CT images, the marker according to the present invention may greatly help to further increase precision and provide more effective medical treatment plans.

The invention is illustrated in greater detail with reference to the following examples and preferred embodiments hereunder.

EXAMPLE 1

A marker formed in a solid silicon cylindrical bar shape with a diameter of 2 mm and a length of 10 cm was prepared.

CT photographing was conducted by use of this marker, and it was found that this marker has sufficient absorption and consequently appears clearly on CT images, which shows it is useful as a CT marker.

EXAMPLE 2

Cosmogel IC00N (polyethylene gel manufactured by Cosmo Instruments Co., Ltd.) was heated up to 130° C. and melted, and then suctioned and filled into a polypropylene tube with an inner diameter of 2 mm and an outer diameter of 3 mm, and then cooled down to prepare a marker with length of 10 cm.

MRI photographing was carried out by use of this marker, and it was found that this marker outputs high signals in both T1-weighted spin-echo images and T2-weighted spin-echo images and accordingly appears clearly on both the images, which shows that it is useful as an MRI marker.

EXAMPLE 3

Example 3 will be described with reference to FIG. 3. Cosmogel IC00N 2 was heated up to 130° C. and melted, and then suctioned and filled into a silicon tube 3 with an inner diameter of 2 mm and an outer diameter of 3 mm, and then cooled down to prepare a marker 1 with a length of 10 cm.

CT photographing was carried out using the marker 1, and it was found that the marker has sufficient absorption and consequently appears clearly on CT images. Furthermore, MRI imaging was carried using the marker 1. As a result, the marker 1 outputs high signals in both T1-weighted spin-echo images and T2-weighted spin-echo images and accordingly appeared clearly on both the images. This single combination marker 1 is thus useful as both a CT marker and an MRI (T1, T2) marker.

EXAMPLE 4

Figure 1:
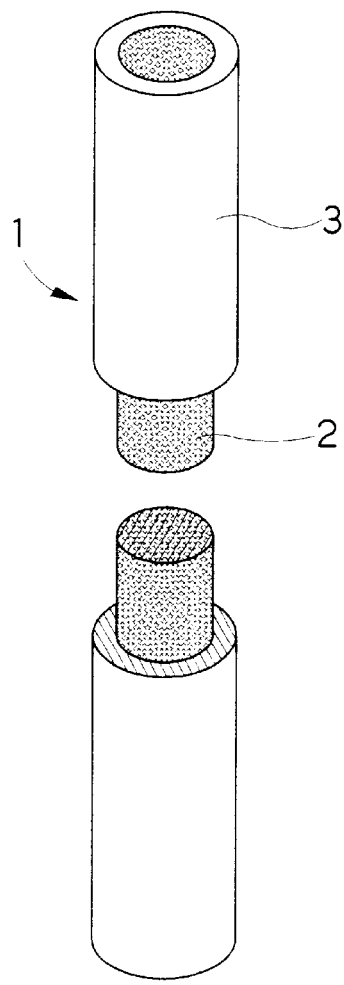
FIG. 1 shows a marker according to a first embodiment of the invention.
Figure 2:
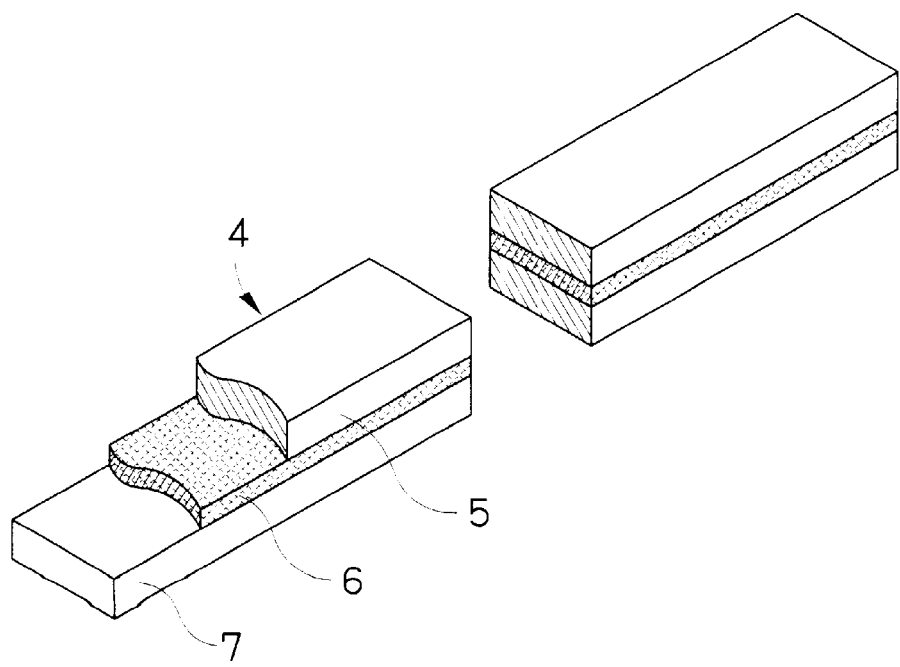
FIG. 2 shows a marker according to a second embodiment of the invention.

Example 4 will be described with reference to FIG. 2. Saivinol AT-304 (acrylic gel manufactured by Saiden Chemical Industry Co., Ltd.) was applied onto a release paper sheet. Its solvent was volatilized, and a dry acrylic gel 6 having a thickness of 500 μm was thereby produced. A silicon sheet having a thickness of 1 mm was then laminated onto the dry acrylic gel. The release paper of acrylic gel was peeled off, and further a silicon sheet having a thickness of 1 mm was attached onto the acrylic gel. Then, the acrylic gel was sandwiched by silicon sheets 5,7, and was cut to form a bar shaped marker 4 with a width of 3 mm and a length of 10 cm.

As a result, the marker 4 outputs high signals to all of CT images by CT photographing, T1-weighted spin-echo images and T2-weighted spin-echo images by MRI photographing and appeared clearly on each of those images. Thus it was found that the marker 4 is useful as both a CT and MRI marker.

As described above, a CT marker according to the present invention shows appropriate X-ray absorption in CT photographing and appears clearly on images. The marker does not cause injury to patients as does the conventional metallic wire used as a marker, and therefore, it is feasible to obtain a marker that may be used in a safer manner for a long period of time.

Furthermore, an MRI marker according to the present invention outputs high signals in both T1-weighted spin-echo images and T2-weighted spin-echo images in MRI photographing and accordingly appears clearly on images. It has excellent storage properties and durability since it is made of an elastomer and/or organogel.

Moreover, combinations of the above CT markers and MRI markers appear clearly on images without interfering with each other in both CT photographing and MRI photographing, and there is consequently no need to exchange markers for each of these photographing operations. Accordingly, it is possible to prevent displacement in both the CT and MRI images. Consequently, as will be appreciated by those skilled in the art, it is feasible to obtain images marked with high precision, and it is thereby feasible to make obtain appropriate and effective medical treatment plans.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description and all changes which come within the meaning and range of equivalency of the claims are therefore intended to be embraced therein.

What is claimed is:

1. A non-implantable CT and MRI marker for CT and MRI imaging, comprising: a hollow bar formed of at least one of a silcone resin and a fluorocarbon resin, being detectable in CT imaging; and an elastomer other than an elastic hydrogel filled and sealed in the hollow bar, being detectable in T1-weighted and T2-weighted MRI imaging.

2. A non-implantable CT and MRI marker according to claim 1; wherein the hollow bar is shaped to be accommodated into a patient restraint apparatus adapted to restrain a patient.

3. A non-implantable CT and MRI marker according to claim 1; wherein the elastomer comprises at least one of styrene isoprene styrene copolymer (SIS), styrene ethylene butylene styrene copolymer (SEBS), styrene ethylene propylene styrene copolymer (SEPS), isoprene rubber (IR), isobutylene isoprene rubber (IIR), and natural rubber (NR).

4. A non-implantable CT and MRI marker according to claim 1; wherein the hollow bar is formed of both the silicone resin and the fluorocarbon resin.

5. A non-implantable CT and MRI marker according to claim 4; further comprising an organogel filled and sealed in the hollow bar.

6. A non-implantable CT and MRI marker according to claim 1; further comprising an organogel filled and sealed in the hollow bar.

7. A non-implantable CT and MRI marker for CT and MRI imaging, comprising: a bar formed of an elastomer other than an elastic hydrogel, being detectable in T1-weighted and T2-weighted MRI imaging; and at least one of a silcone resin and a fluorocarbon resin covering at least a portion of a circumference of the bar, being detectable in CT imaging.

8. A non-implantable CT and MRI marker according to claim 7; wherein the elastomer comprises at least one of styrene isoprene styrene copolymer (SIS), styrene ethylene butylene styrene copolymer (SEBS), styrene ethylene propylene styrene copolymer (SEPS), isoprene rubber (IR), isobutylene isoprene rubber (IIR), and natural rubber (NR).

9. A non-implantable CT and MRI marker according to claim 7; wherein the bar is formed of both the elastomer and an organogel.

10. A non-implantable CT and MRI marker according to claim 9; wherein both the silicone resin and the fluorocarbon resin cover the portion of the circumference of the bar.

11. A non-implantable CT and MRI marker according to claim 7; wherein both the silicone resin and the fluorocarbon resin cover the portion of the circumference of the bar.

12. A non-implantable CT and MRI marker for CT and MRI imaging, comprising: a hollow bar formed of at least one of a silicone resin and a fluorocarbon resin, being detectable in CT imaging; and a organogel filled and sealed in the hollow bar, being detectable in T1-weighted and T2-weighted MRI imaging.

13. A non-implantable CT and MRI marker according to claim 12; wherein the organogel comprises at least one of polyethylene gel, acrylic gel and urethane gel.

14. A non-implantable CT and MRI marker according to claim 13; wherein the polyethylene gel comprises a plasticizer mixed into ethylene styrene copolymer.

15. A non-implantable CT and MRI marker according to claim 14; wherein the plasticizer comprises one of liquid paraffin, mineral oil, a phthalic acid plasticizer, soy bean oil, and a fatty acid.

16. A non-implantable CT and MRI marker according to claim 15; wherein the phthalic acid plasticizer comprises one of butyl benzyl phthalate (BBP), di-octyle phthalate (DOP), di-butyl phthalate (DBP), and di-isononyl phthalate (DINP).

17. A non-implantable CT and MRI marker according to claim 15; wherein the fatty acid comprises one of oleic acid and linoleic acid.

18. A non-implantable CT and MRI marker according to claim 13; wherein the acrylic gel is copolymerized by a main component comprising one of 2-ethyl hexyl acrylate, methyl acrylate, methyl methacrylate and butyl acrylate, and one of acrylic acid, methacrylic acid and vinyl acetate.

19. A non-implantable CT and MRI marker according to claim 18; further comprising a plasticizer crosslinked by a chemical compound selected from the group consisting of isocyanate, aziridine and an epoxy.

20. A non-implantable CT and MRI marker according to claim 13; wherein the urethane gel comprises one of a gel of a urethane resin plasticized by a phthalic acid type plasticizer and a gel of urethane resin polymerized by polyisocyanate and polyole with a molecular weight above about 3000.

21. A non-implantable CT and MRI marker for CT and MRI imaging, comprising: a bar formed of an organogel, being detectable in T1-weighted and T2-weighted MRI imaging; and at least one of a silicone resin and a fluorocarbon resin covering at least a portion of a circumference of the bar, being detectable in CT imaging.

22. A non-implantable CT and MRI marker according to claim 21; wherein the organogel comprises at least one of polyethylene gel, acrylic gel and urethane gel.

23. A non-implantable CT and MRI marker according to claim 22; wherein the polyethylene gel comprises a plasticizer mixed into ethylene styrene copolymer.

24. A non-implantable CT and MRI marker according to claim 23; wherein the plasticizer comprises one of liquid paraffin, mineral oil, a phthalic acid plasticizer, soy bean oil, and a fatty acid.

25. A non-implantable CT and MRI marker according to claim 24; wherein the phthalic acid plasticizer comprises one of butyl benzyl phthalate (BBP), di-octyle phthalate (DOP), di-butyl phthalate (DBP), and di-isononyl phthalate (DINP).

26. A non-implantable CT and MRI marker according to claim 24; wherein the fatty acid comprises one of oleic acid and linoleic acid.

27. A non-implantable CT and MRI marker according to claim 22; wherein the acrylic gel is copolymerized by a main component comprising one of 2-ethyl hexyl acrylate, methyl acrylate, methyl methacrylate and butyl acrylate, and one of acrylic acid, methacrylic acid and vinyl acetate.

28. A non-implantable CT and MRI marker according to claim 27; further comprising a plasticizer crosslinked by a chemical compound selected from the group consisting of isocyanate, aziridine and an epoxy.

29. A non-implantable CT and MRI marker according to claim 22; wherein the urethane gel comprises one of a gel of a urethane resin plasticized by a phthalic acid type plasticizer and a gel of urethane resin polymerized by polyisocyanate and polyole with a molecular weight above about 3000.

30. A non-implantable CT and MRI marker for CT and MRI imaging, comprising: a first component comprised of a pair of overlapping members and formed of at least one a silcone resin and a fluorocarbon resin, being detectable in CT imaging; and a second component comprised of at least one of an elastomer other than an elastic hydrogel and an organogel disposed between the overlapping members, being detectable in T1-weighted and T2-weighted MRI imaging.

31. A non-implantable CT and MRI marker according to claim 30; wherein the first component is formed of both the silicone resin and the fluorocarbon resin.

32. A non-implantable CT and MRI marker according to claim 31; wherein the second component is comprised of both the elastomer and the organogel.

33. A non-implantable CT and MRI marker according claim 30; wherein the second component is comprised of both the elastomer and the organogel.

* * * * *